United States Patent [19]

Kühle et al.

[11] Patent Number: 4,737,522

[45] Date of Patent: Apr. 12, 1988

[54] N-SULPHENYLATED BENZENESULPHONIC ACID AMIDE FUNGICIDES

[75] Inventors: Engelbert Kühle, Bergisch-Gladbach; Hans-Georg Schmitt, Krefeld; Wilhelm Brandes, Leichlingen; Paul Reinecke, Leverkusen, all of Fed. Rep. of Germany

[73] Assignee: Bayer Aktiengesellschaft, Leverkusen, Fed. Rep. of Germany

[21] Appl. No.: 898,673

[22] Filed: Aug. 21, 1986

[30] Foreign Application Priority Data

Sep. 3, 1985 [DE] Fed. Rep. of Germany ....... 3531362

[51] Int. Cl.$^4$ ...................... A01N 41/06; C07C 143/80

[52] U.S. Cl. ...................................... 514/603; 564/87; 564/91; 514/604

[58] Field of Search .................................. 564/91, 87; 514/603–604

[56] References Cited

U.S. PATENT DOCUMENTS 3,285,929 11/1966 Klauke et al. ......................... 564/91

FOREIGN PATENT DOCUMENTS 1193498 5/1965 Fed. Rep. of Germany .

994603 6/1965 United Kingdom .................. 564/91

*Primary Examiner*—Anton H. Sutto

*Attorney, Agent, or Firm*—Sprung Horn Kramer & Woods

[57] ABSTRACT

Fungicidally active novel N-sulphenylated benzene sulphonic acid amides of the formula

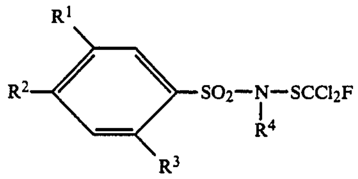

in which $R^1$, $R^2$ and $R^3$ independently of one another represent hydrogen, halogen, nitro, alkyl or halogenoalkyl and $R^4$ represents alkyl, alkenyl, halogenoalkinyl, cycloalkyl which is optionally substituted by alkyl, alkoxyalkyl or alkylthioalkyl, excluding the compounds in which (a) $R^4$ represents methyl and (i) $R^1$, $R^2$ and $R^3$ represents hydrogen, or (ii) $R^1$ represents chlorine or nitro, $R^2$ represents chlorine and $R^3$ represents hydrogen, or (iii) $R^1$ represents nitro and $R^2$ and $R^3$ represent hydrogen, or (iv) $R^1$ and $R^3$ represent chlorine and $R^2$ represents hdyrogen and (b) $R^4$ represents n-butyl, $R^1$ and $R^3$ represent hydrogen and $R^2$ represents chlorine.

11 Claims, No Drawings

N-SULPHENYLATED BENZENESULPHONIC ACID AMIDE FUNGICIDES

The present invention relates to new N-sulphenylated benzenesulphonic acid amides, a process for their preparation and their use as fungicides in plant protection.

It has been known for a long time that N-trihalogenomethylthio compounds can be used as fungicides in agriculture and horticulture. Thus, for example, N-(trichloromethylthio)-tetrahydrophthalimide (German Patent Specification No. 887,506) and N,N-dimethyl-N'-phenyl-N'-(dichlorofluoromethylthio)-sulphamide (German Patent Specification No. 1,193,498) are used in practice in pomiculture and viticulture for combating fungal diseases. N-(Dichlorofluoromethylthio)-benzenesulphonamides, such as, for example, N-dichlorofluoromethylthio-N-methyl-3,4-dichlorobenzene- and -3-nitrobenzenesulphonamide, are furthermore also known (compare likewise German Patent Specification No. 1,193,498).

New N-sulphenylated benzenesulphonic acid amides of the general formula (I)

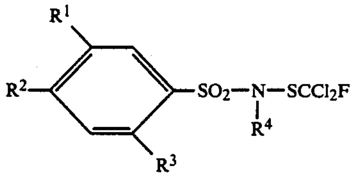

(I)

in which $R^1$, $R^2$ and $R^3$ independently of one another represent hydrogen, halogen, nitro, alkyl or halogenoalkyl and $R^4$ represents alkyl, alkenyl, halogenoalkinyl, cycloalkyl which is optionally substituted by alkyl, alkoxyalkyl or alkylthioalkyl, excluding the compounds in which (a) $R^4$ represents methyl and (i) $R^1$, $R^2$ and $R^3$ represent hydrogen, or (ii) $R^1$ represents chlorine or nitro, $R^2$ represents chlorine and $R^3$ represents hydrogen, or (iii) $R^1$ represents nitro and $R^2$ and $R^3$ represent hydrogen, or (iv) $R^1$ and $R^3$ represent chlorine and $R^2$ represents hydrogen and (b) $R^4$ represents n-butyl, $R^1$ and $R^3$ represent hydrogen and $R^2$ represents chlorine, have been found.

It has furthermore been found that the N-sulphenylated benzenesulphonamides of the general formula (I)

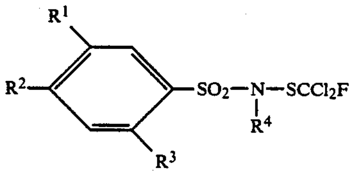

(I)

in which $R^1$, $R^2$ and $R^3$ independently of one another represent hydrogen, halogen, nitro, alkyl or halogenoalkyl and $R^4$ represents alkyl, alkenyl, halogenoalkinyl, cycloalkyl which is optionally substituted by alkyl, alkoxyalkyl or alkylthioalkyl, excluding the compounds in which (a) $R^4$ represents methyl and (i) $R^1$, $R^2$ and $R^3$ represent hydrogen, or (ii) $R^1$ represents chlorine or nitro, $R^2$ represents chlorine and $R^3$ represents hydrogen, or (iii) $R^1$ represents nitro and $R^2$ and $R^3$ represent hydrogen, or (iv) $R^1$ and $R^3$ represent chlorine and $R^2$ represents hydrogen and (b) $R^4$ represents n-butyl, $R^1$ and $R^3$ represent hydrogen and $R^2$ represents chlorine, are obtained by a process in which benzenesulphonamides of the general formula (II)

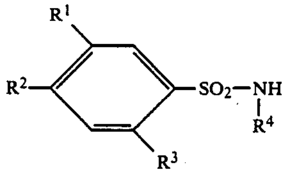

(II)

in which the radicals $R^1$ to $R^4$ have the abovementioned meaning, are reacted with dichlorofluoromethanesulphenyl chloride of the formula (III)

$Cl—SSCl_2F$ (III)

in the presence of an acid-binding agent and if appropriate in the presence of a diluent.

According to the invention, halogen in the definitions of $R^1$, $R^2$ and $R^3$ denotes fluorine, chlorine, bromine or iodine, preferably fluorine, chlorine or bromine and particular bromine or chlorine.

Alkyl in the definitions of $R^1$, $R^2$ and $R^3$ denotes straight-chain or branched alkyl with 1 to 4 carbon atoms, preferably with 1 to 3 and in particular with 1 or 2 carbon atoms. Radicals which may be mentioned are methyl, ethyl, n-propyl, iso-propyl, n-butyl, sec.-butyl and tert.-butyl.

Halogenoalkyl in the definitions $R^1$, $R^2$ and $R^3$ denotes straight-chain or branched alkyl which has 1 to 4 carbon atoms, preferably 1 to 3 and in particular 1 or 2 carbon atoms, and is substituted by 1 to 5 halogen atoms. Halogen denotes fluorine, chlorine, bromine or iodine, preferably fluorine, chlorine or bromine and in particular fluorine and/or chlorine. Radicals which may be mentioned are trifluoromethyl, trichloromethyl, dichlorofluoromethyl and dichlorofluoroethyl.

Alkyl in the definition $R^4$ denotes straight-chain or branched alkyl with 1 to 8 carbon atoms, preferably with 1 to 6 and in particular with 1 to 5 carbon atoms. Radicals which may be mentioned are methyl, ethyl, n-propyl, iso-propyl, n-butyl, iso-butyl, tert.-butyl, n-pentyl, n-hexyl, n-heptyl and n-octyl.

Alkenyl in the definition of $R^4$ denotes alkenyl with 3 to 6 carbon atoms, preferably with 3 to 5 carbon atoms. Radicals which may be mentioned are allyl, crotyl, pentenyl and hexenyl.

Halogenoalkinyl in the definition of $R^4$ denotes alkinyl which has 3 to 6 carbon atoms, preferably 3 to 5 and in particular 3 or 4 carbon atoms, and is substituted by 1 to 3 halogen atoms. Halogen denotes fluorine, chlorine, bromine or iodine, preferably chlorine or iodine and in particular iodine. Radicals which may be mentioned are iodopropargyl and iodobutinyl.

Cycloalkyl in the definition of $R^4$ which is optionally mono-, di-, tri- or tetrasubstituted by alkyl denotes monocyclic with 3 to 8 ring-carbon atoms, preferably 3 to 7 and in particular 5 or 6 ring-carbon atoms, The substituent alkyl in this connection denotes straight-chain or branched alkyl with 1 to 4 carbon atoms, preferably 1 to 3 and in particular 1 or 2 carbon atoms. Radicals which may be mentioned are methyl, ethyl, n-propyl, iso-propyl, n-butyl, iso-butyl and tert.-butyl.

Radicals which may be mentioned are cyclopropyl, cyclobutyl, cyclopentyl, cyclohexyl, cycloheptyl, 3,3,5-trimethylcyclohexyl, 4-methylcyclohexyl and 2-methylcyclopentyl.

Alkoxyalkyl and alkylthioalkyl in the definition of $R^4$ denotes alkoxy- or alkylthioalkyl with 1 to 6 carbon atoms per alkoxy, and alkylthio and 2–6 carbon atoms in the alkyl part, preferably with 1 to 4 and in particular with 1 to 3 carbon atoms per alkoxy and alkylthio and 2–4, in particular 2 or 3 carbon atoms in the alkyl part. Radicals which may be mentioned are methoxyethyl, methoxy-n-propyl, methoxy-n-butyl, ethoxyethyl, ethoxy-n-propyl, ethoxy-n-butyl, n-propoxyethyl, n-propoxy-n-propyl, n-propoxy-n-butyl and n-butoxy-n-butyl, methylthioethyl, methylthio-n-propyl, methylthio-n-butyl, ethylthioethyl, ethylthio-n-propyl, ethylthio-n-butyl, n-propylthio-n-butyl and n-butylthio-n-butyl.

The N-sulphenylated benzenesulphonic acid amides of the formula (I) according to the invention have a good fungicidal activity in plant protection, coupled with a good plant tolerance.

Surprisingly, the compounds according to the invention thereby exhibits a considerably more powerful fungicidal activity than the compounds known from the prior art, which are very closely related compounds structurally, and from the point of view of their action.

Formula (I) provides a general definition of the N-sulphenylated benzenesulphonic acid amides according to the invention. Preferred compounds are those in which $R^1$, $R^2$ and $R^3$ independently of one another represent hydrogen, fluorine, chlorine, bromine, alkyl with 1 to 3 carbon atoms or halogenoalkyl with 1 to 3 carbon atoms and 1 to 5 halogen atoms, preferably fluorine and chlorine, and $R^4$ represents alkyl with 1 to 6 carbon atoms, alkenyl with 3 to 5 carbon atoms, halogenoalkinyl with 1 to 3 chlorine or iodine atoms and 3 to 5 carbon atoms, monocyclic cycloalkyl which has 3 to 7 carbon atoms and is optionally mono-, di-, tri- or tetrasubstituted by alkyl with 1 to 3 carbon atoms or alkoxyalkyl or alkylthioalkyl with 1 to 4 carbon atoms per alkoxy and alkylthio and 2–4 carbon atoms in the alkyl part, excluding the compounds in which (a) $R^4$ represents methyl and (i) $R^1$, $R^2$ and $R^3$ represent hydrogen, or (ii) $R^1$ represents chlorine or nitro, $R^2$ represents chlorine and $R^3$ represents hydrogen, or (iii) $R^1$ represents nitro and $R^2$ and $R^3$ represent hydrogen, or (iv) $R^1$ and $R^3$ represent chlorine and $R^2$ represents hydrogen and (b) $R^4$ represents n-butyl, $R^1$ and $R^3$ represent hydrogen and $R^2$ represents chlorine.

Particularly preferred compounds of the formula (I) are those in which $R^1$, $R^2$ and $R^3$ independently of one another represent hydrogen, bromine, chlorine, alkyl with 1 or 2 carbon atoms or halogenoalkyl with 1 or 2 carbon atoms and 1 to 5 fluorine atoms and $R^4$ represents alkyl with 1 to 5 carbon atoms, or represents alkenyl with 3 to 5 carbon atoms, halogenoalkinyl with 3 or 4 carbon atoms and 1 to 3 iodine atoms, monocyclic cycloalkyl which has 5 or 6 ring-carbon atoms and is optionally mono-, di-, tri- or tetrasubstituted by methyl or ethyl or alkoxyalkyl or alkylthioalkyl with 1 to 3 carbon atoms per alkoxy and alkylthio and 2 or 3 carbon atoms in the alkyl part, excluding the compounds in which (a) $R^4$ represents methyl and (i) $R^1$, $R^2$ and $R^3$ represent hydrogen, or (ii) $R^1$ represents chlorine or nitro, $R^2$ represents chlorine and $R^3$ represents hydrogen, or (iii) $R^1$ represents nitro and $R^2$ and $R^3$ represent hydrogen, or (iv) $R^1$ and $R^3$ represent chlorine and $R^2$ represents hydrogen, and (b) $R^4$ represents n-butyl, $R^1$ and $R^3$ represent hydrogen and $R^2$ represents chlorine.

Compounds of the formula (I) which are furthermore particularly preferred are those in which $R^1$, $R^2$ and $R^3$ independently of one another represent hydrogen, chlorine, nitro or methyl and $R^4$ represents methyl, ethyl, iso-propyl, n-butyl, iodopropargyl, cyclopentyl, cyclohexyl, allyl or 3-methoxy-n-propyl, excluding the compounds in which (a) $R^4$ represents methyl and (i) $R^1$, $R^2$ and $R^3$ represent hydrogen, or (ii) $R^1$ represents chlorine or nitro, $R^2$ represents chlorine and (iii) $R^3$ represents hydrogen, or $R^1$ represents nitro and $R^2$ and $R^3$ represent hydrogen, or (iv) $R^1$ and $R^3$ represent chlorine and $R^2$ represents hydrogen and (b) $R^4$ represents n-butyl, $R^1$ and $R^3$ represent hydrogen and $R^2$ represents chlorine.

In addition to the preparation examples, the following N-sulphenylated benzenesulphonic acid amides of the formula (I) may be mentioned specifically:

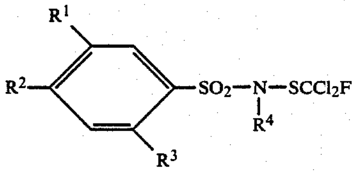

(I)

| $R^1$ | $R^2$ | $R^3$ | $R^4$ |
|---|---|---|---|
| H | H | H | $C_2H_5$ |
| H | H | H | $C_3H_7$—i |
| H | H | H | $C_4H_9$—i |
| H | H | H | $C_4H_9$—t |
| H | H | H | $CH_2C(CH_3)_3$ |
| H | Cl | H | $C_3H_7$—n |
| H | Cl | H | $C_3H_7$—n |
| H | Cl | H | $CH_2CH{=}CH_2$ |
| Cl | H | H | $CH_3$ |
| Cl | H | H | 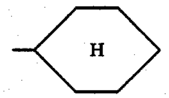 |
| H | $CH_3$ | H | $CH_3$ |
| H | $CH_3$ | H | $C_4H_9$—n |
| H | $CH_3$ | H | 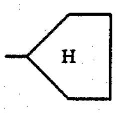 |
| H | $CH_3$ | H | 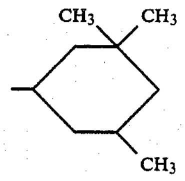 |

-continued

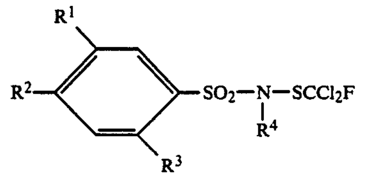

(I)

| $R^1$ | $R^2$ | $R^3$ | $R^4$ |
|---|---|---|---|
| H | $CF_3$ | H | $CH_3$ |
| H | $CF_3$ | H | $C_2H_5$ |
| $NO_2$ | H | H | $CH_3$ |
| H | $NO_2$ | H | $CH_3$ |
| H | $NO_2$ | H | 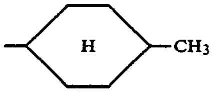 |

If, for example, 4-methylbenzenesulphonic acid methylamide and dichlorofluoromethanesulphenyl chloride are used as starting components, the course of the reaction can be represented by the following equation:

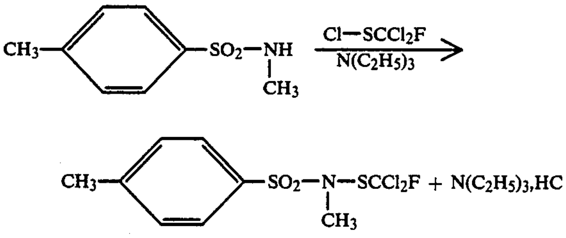

Formula (II) provides a general definition of the benzenesulphonic acid amides required as starting substances. In this formula, $R^1$ to $R^4$ preferably have the meanings which have been mentioned for these substituents in the description of the compounds of the formula I according to the invention.

The benzenesulphonic acid amides of the formula (II) are known or are obtainable in a manner which is known per se, in which benzenesulphonyl chlorides of the formula (IV)

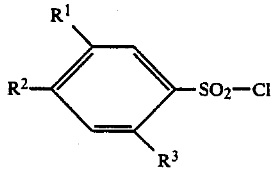

(IV)

in which $R^1$ to $R^3$ have the meaning given in the case of formula (I), are reacted with a primary amine of the formula (V)

$R^4$—$NH_2$ (V)

in which $R^4$ has the abovementioned meaning, if appropriate in the presence of a base and a diluent.

Formula (IV) provides a general definition of the benzenesulphonyl chlorides required as starting materials. In this formula, $R^1$ to $R^3$ preferably have the meanings which have already been mentioned in connection with formula (I).

Examples of suitable benzenesulphonyl chlorides are benzene-, 4-toluene-, 2-, 3- or 4-chlorobenzene-, 3,4-dichlorobenzene-, 3- or 4-nitrobenzene- and 3-trifluoromethyl-4-chlorobenzenesulphonyl chloride.

Formula (V) provides a general definition of the amines required as starting substances. In this formula, $R^4$ preferably has the meanings which have already been mentioned in connection with formula (I).

Examples of suitable amines of the formula (V) are methyl-, ethyl-, isopropyl-, tert.-butyl-, allyl-, methoxyethyl-, methylmercaptoethyl-, propargyl-, cyclopentyl-, cyclohexyl- and 4-methylcyclohexyl-amine.

The benzenesulphonylpropargylamide can be converted into the 3-iodopropargylamides by iodination in an alkaline medium.

The dichlorofluoromethanesulphenyl chloride of the formula (III) is known from the literature (compare, for example, Ang. Chem. 76, 807 (1964)).

Possible diluents in carrying out the process according to the invention are all the inert organic solvents. These include, preferably, hydrocarbons, such as toluene; chlorohydrocarbons, such as methylene chloride and chlorobenzene, or ethers, such as dioxane, and water.

Acid-binding agents which can be used are inorganic bases, such as sodium hydroxide and sodium carbonate, or tert.-amines, such as pyridine and triethylamine.

The reaction temperature can be varied within a substantial range. The reaction is in general carried out at from 0° to 100° C., preferably 20° to 50° C.

The process according to the invention is carried out as follows: a benzenesulphonic acid amide of the formula (II) and the sulphenyl chloride of the formula (III) are initially taken in a diluent. The acid-binding agent is added in portions at room temperature, so that the reaction temperature rises to about 40° C. When the reaction has ended, the N-sulphenylated benzenesulphonic acid amide of the formula (I) is precipitated with water and isolated and purified in the customary manner (distillation or crystallization).

The active compounds according to the invention exhibit a powerful microbicidal action and can be employed in practice for combating undesired micro-organisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which fall under the generic names listed above may be mentioned as examples but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubense;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. gramine;* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae;* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules and latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussion Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing and the like. It is furthermore possible to apply the active compounds by the ultra low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

The good fungicidal action against rust, Septoria and Cochliobolus sativus in cereals, the good fungicidal action in the agar plate test and the bactericidal action may also be mentioned.

PREPARATION EXAMPLES

EXAMPLE 1

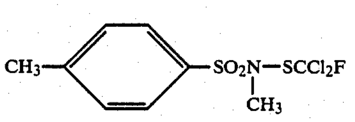

18.5 g (0.1 mole) of 4-toluenesulphonic acid N-methylamide are dissolved in 100 ml of toluene with the addition of 16.9 g (0.1 mole) of dichlorofluoromethanesulphenyl chloride, and a solution of 11.2 g (0.11 mole) of triethylamine in 20 ml of toluene is added at room temperature. The temperature thereby rises to about 50° C. Water is added, the layers are separated and the toluene solution is concentrated in vacuo, after being dried. The residue (27 g; $n_D^{20}$: 1.5528) is distilled under a high vacuum. 21 g (66% of theory) of the desired substance are obtained with the following physical data: $Kp_{0.15}$: 150° to 155° C., $n_D^{20}$ 1.5519, melting point 42° to 43° C.

Compounds of the formula (I)

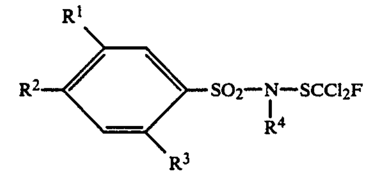

(I)

are obtained in an analogous manner:

| Example | $R^1$ | $R^2$ | $R^3$ | $R^4$ | Physical data: melting point (°C.); $n_D^{20}$: ; Boiling point (°C./mm Hg) |
|---|---|---|---|---|---|
| 2 | H | H | H | $C_2H_5$ | 133-40/0.2 |
| 3 | H | H | H | $C_4H_9$—n | 140-45/0.1 |
| 4 | H | $CH_3$ | H | $C_2H_5$ | 153-58/0.2 |
| 5 | H | $CH_3$ | H | $C_4H_9$—n | 168-69/0.15 |
| 6 | H | Cl | H | $C_2H_5$ | 170-75/0.2 |
| 7 | $NO_2$ | $CH_3$ | H | $CH_3$ | 69-70 |
| 8 | $NO_2$ | $CH_3$ | H | $C_4H_9$—n | 56-58 |
| 9 | $NO_2$ | H | $CH_3$ | $C_4H_9$—n | 86-88 |
| 10 | H | H | $NO_2$ | $C_4H_9$—n | 76-78 |
| 11 | $NO_2$ | H | H | $C_4H_9$—n | 62 |
| 12 | $NO_2$ | Cl | H | $C_4H_9$—n | 74-75 |
| 13 | H | $NO_2$ | H | $CH_3$ | 107-108 |
| 14 | H | $NO_2$ | H | $C_4H_9$—n | 1.5574 |
| 15 | $NO_2$ | H | Cl | $C_4H_9$—n | 57-58 |
| 16 | $CH_3$ | $CH_3$ | H | $CH_3$ | Cl calculated 21.4 found 21.4 |
| 17 | $CH_3$ | $CH_3$ | H | $C_3H_7$—i | 78-80 |
| 18 | $CH_3$ | H | $CH_3$ | $CH_3$ | 79 |
| 19 | H | $CH_3$ | H | $C_6H_{11}$ | 89-90 |
| 20 | H | $CH_3$ | H | $C_3H_5$ | 1.5536 |
| 21 | H | $CH_3$ | H | —$CH_2CH_2CH_2$—$OCH_3$ | 1.5396 |
| 22 | H | $CH_3$ | H | 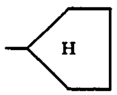 | 1.5683 |

EXAMPLE 23

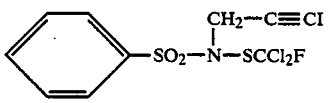

0.1 mole of N-iodopropargylbenzenesulphonamide is dissolved in tetrahydrofuran, 18.6 g (0.11 mole) of dichlorofluoromethanesulphenyl chloride are added and the solution is cooled to 0° C. 11 g (0.11 mole) of triethylamine are slowly added dropwise at this temperature. The mixture is allowed to come slowly to room temperature and is then warmed at 60° C. for 1 hour. The solvent is stripped off in vacuo, the residue is taken up in methylene chloride and the organic phase is washed with water. After drying over sodium sulphate, the solvent is stripped off and the residue which remains is taken up in cyclohexane. The undissolved starting substance is separated off and the solution is concentrated on a rotary evaporator. The oil which initially remains crystallizes in a refrigerator.

Melting point: 82°-84° C.

The following compounds are obtained analogously:

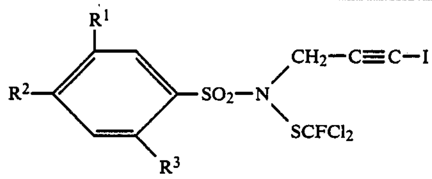

| Example | $R^1$ | $R^2$ | $R^3$ | Physical data melting point (°C.) |
|---|---|---|---|---|
| 24 | H | H | H | 82-84 |
| 25 | H | $CH_3$ | H | 106-108 |
| 26 | H | Cl | H | 99-101 |
| 27 | Cl | Cl | H | 81-83 |

Preparation of the precursors

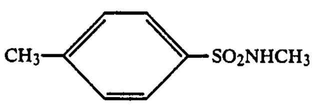

V1

38 g (0.2 mole) of 4-toluenesulphonyl chloride, dissolved in 125 ml of toluene, are charged with 13 g (0.4 mole) of gaseous methylamine at 20°-30° C., while cooling. The reaction product and methylammonium chloride precipitate out immediately. The precipitate is filtered off with suction, washed with water and dried. 32 g (86.5% of theory) of the desired product are obtained with a melting point of 77°-79° C.

The following sulphonamides of the formula (II) are prepared analogously:

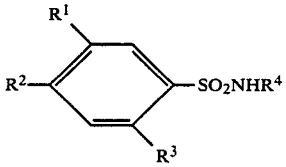

(II)

| Example | $R^1$ | $R^2$ | $R^3$ | $R^4$ | Physical data: Melting point (°C.); $n_D^{20}$: ; Boiling point (°C./mm Hg) |
|---|---|---|---|---|---|
| V2 | H | H | H | $C_2H_5$ | 54-55 |
| V3 | H | H | H | $C_4H_9$—n | 1,5238 |
| V4 | H | $CH_3$ | H | $C_2H_5$ | 63-64 |
| V5 | H | $CH_3$ | H | $C_4H_9$—n | 41-43 |
| V6 | H | Cl | H | $C_2H_5$ | 70-71 |
| V7 | $NO_2$ | $CH_3$ | H | $CH_3$ | 69-70 |
| V8 | $NO_2$ | $CH_3$ | H | $C_4H_9$—n | 56-58 |
| V9 | $NO_2$ | H | $CH_3$ | $C_4H_9$—n | 86-88 |
| V10 | H | H | $NO_2$ | $C_4H_9$—n | 76-78 |
| V11 | $NO_2$ | H | H | $C_4H_9$—n | 62-63 |
| V12 | $NO_2$ | Cl | H | $C_4H_9$—n | 74-75 |
| V13 | H | $NO_2$ | H | $CH_3$ | 102-104 |
| V14 | H | $NO_2$ | H | $C_4H_9$—n | 78-80 |
| V15 | $NO_2$ | H | Cl | $C_4H_9$—n | 135-136 |
| V16 | $CH_3$ | $CH_3$ | H | $CH_3$ | oil |
| V17 | $CH_3$ | $CH_3$ | H | $C_3H_7$i | oil |
| V18 | $CH_3$ | H | $CH_3$ | $CH_3$ | 84-85 |
| V19 | H | $CH_3$ | H | $C_6H_{11}$ | 85-86 |
| V20 | H | $CH_3$ | H | $C_3H_5$ | 63-65 |
| V21 | H | $CH_3$ | H | —$CH_2$—$CH_2$—$CH_2$—$OCH_3$ | 1.5242 |

-continued (II)

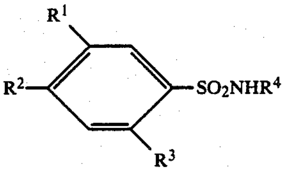

| Example | $R^1$ | $R^2$ | $R^3$ | $R^4$ | Physical data: Melting point (°C.); $n_D^{20}$: ; Boiling point (°C./mm Hg) |
|---|---|---|---|---|---|
| V22 | H | $CH_3$ | H | 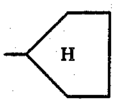 | 82–84 |

EXAMPLE V23

(a)

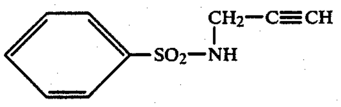

0.1 mole of phenylsulphonyl chloride, dissolved in a little tetrahydrofuran, is added dropwise to a solution of 6 g (0.11 mole) of propargylamine and 11 g (0.11 mole) of triethylamine in 50 ml of tetrahydrofuran at room temperature. The mixture is then heated overnight under reflux, the solvent is distilled off and the residue is taken up in water. The solid product is filtered off with suction, washed with water and dried in air. Any residues of unreacted sulphochloride can be removed by washing the filter cake with cyclohexane or petroleum ether.

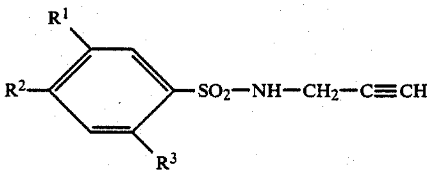

| Example | $R^1$ | $R^2$ | $R^3$ | Physical data: Melting point (°C.) |
|---|---|---|---|---|
| VV24 | H | H | H | 73–74 |
| VV25 | H | $CH_3$ | H | 68–70 |
| VV26 | H | Cl | H | 45–47 |
| VV27 | Cl | Cl | H | 98–100 |

(b)

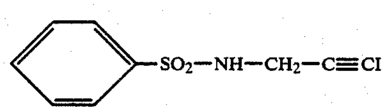

0.1 ml of N-propargylphenylsulphonamide is dissolved in 250 ml of methanol. After the solution has been cooled to −10° C., 75 g of 25% strength sodium hydroxide soluton are added dropwise so that the temperature remains below 0° C. 34 g of iodine are then added in portions at 0° to 5° C. in the course of 5 minutes. Stirring is continued at 0° to 5° C. for 2 hours and the solvent is then stripped off completely in vacuo at temperatures <25° C. The residue is taken up in water, the pH is brought to 3 with dilute hydrochloric acid and the mixture is decolorized with 10% strength sodium bisulphite solution. After the suspension has been filtered with suction, the crystals are washed with water and dried in vacuo.

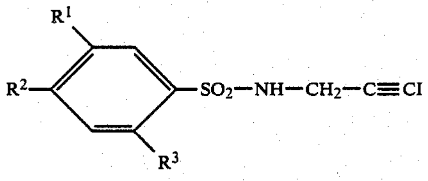

| Example | $R^1$ | $R^2$ | $R^3$ | Physical data: Melting point (°C.) |
|---|---|---|---|---|
| V24 | H | H | H | 81–83 |
| V25 | H | $CH_3$ | H | 124–125 |
| V26 | H | Cl | H | 119–120 |
| V27 | Cl | Cl | H | 104–105 |

Use Examples

The compounds shown below are used as comparison substances in the use examples which follow:

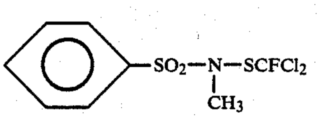

(A)

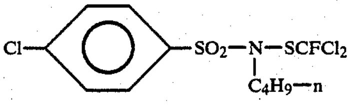

(B)

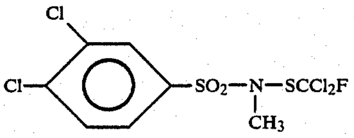

(C)

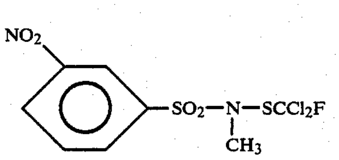

(D)

All the compounds are known from German Patent Specification No. 1,193,498.

EXAMPLE A

Phytophthora Test (tomato)/protective

Solvent: 4.7 parts by weight of acetone

Emulsifier: 0.3 parts by weight of alkylaryl polyglycol ether

To produce a suitable preparation of active compound, 1 part by weight of active compound is mixed with the started amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans.*

The plants are placed in an incubation cabinet at 100% relative atmospheric humidity and at about 20° C.

Evaluation is carried out 3 days after the inoculation.

In this test, a clearly superior activity compared with the prior art is shown, for example, by the compounds of preparation Examples 11, 18, 23, 27 and 13.

EXAMPLE B

*Drechslera graminea* test (barley)/seed treatment (syn. *Helminthosporium gramineum*)

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

The seed is embedded in sieved, moist standard soil and is exposed to a temperature of 4° C. in closed Petri dishes in a refrigerator for 10 days. Germination of the barley, and possibly also of the fungus spores, is thereby initiated. 2 batches of 50 grains of the pregerminated barley are subsequently sown 3 cm deep in standard soil and are cultivated in a greenhouse at a temperature of about 18° C., in seedboxes which are exposed to light for 15 hours daily.

About 3 weeks after sowing, the plants are evaluated for symptoms of stripe disease.

In this test, a clearly superior activity compared with the prior art is shown, for example, by the compounds of preparation Examples 2, 1, 4, 5, 6 and 16.

EXAMPLE C

*Pyrenophora teres* test (barley)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Pyrenophora teres.* The plants the remain in an incubation cabinet at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds of preparation Examples 7, 10, 11, 13, 14, 15, and 27.

It is understood that the specification and examples are illustrative but not limitative of the present invention and that other embodiments within the spirit and scope of the invention will suggest themselves to those skilled in the art.

We claim:

1. An N-sulphenylated benzenesulphonic acid amide of the formula

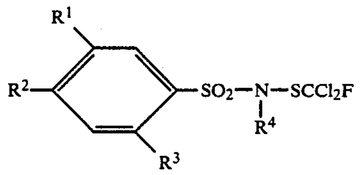

in which $R^1$, $R^2$ and $R^3$ independently of one another represent hydrogen, fluorine, chlorine, bromine, nitro, alkyl with 1 to 3 carbon atoms or halogenoalkyl with 1 to 3 carbon atoms and 1 to 5 halogen atoms, and $R^4$ represents alkyl with 1 to 6 carbon atoms, alkenyl with 3 to 5 carbon atoms, halogenoalkinyl with 1 to 3 chlorine or iodine atoms and 3 to 5 carbon atoms, monocyclic cycloalkyl which has 3 to 7 carbon atoms and is optionally mono-, di-, tri- or tetrasubstituted by alkyl with 1 to 3 cabon atoms or alkoxyalkyl or alkylthioalkyl with 1 to 4 carbon atoms per alkoxy and alkylthio and 2–4 carbon atoms in the alkyl part, excluding the compounds in which (a) $R^4$ represents methyl and (i) $R^1$, $R^2$ and $R^3$ represent hydrogen, or (ii) $R^1$ represents chlorine or nitro, $R^2$ represents chlorine and $R^3$ represents hydrogen, or (iii) $R^1$ represents nitro and $R^2$ and $R^3$ represent hydrogen, or (iv) $R^1$ and $R^3$ represent chlorine and $R^2$ represents hydrogen and (b) $R^4$ represents n-butyl, $R^1$ and $R^3$ represent hydrogen and $R^2$ repesents chlorine.

2. A method of combating fungi which comprises applying to such fungi or to a fungus habitat a fungicidally effective amount of a compound according to claim 1.

3. An N-sulphenylated benzenesulphonic acid amide according to claim 1 in which $R^1$, $R^2$ and $R^3$ independently of one another represent hydrogen, bromine, chlorine, alkyl with 1 or 2 carbon atoms or halogenoalkyl with 1 or 2 carbon atoms and 1 to 5 fluorine atoms and $R^4$ represents alkyl with 1 to 5 carbon atoms, or represents alkenyl with 3 to 5 carbon atoms, halogenoalkinyl with 3 or 4 carbon atoms and 1 to 3 iodine atoms, monocyclic cycloalkyl which has 5 or 6 carbon atoms and is optionally mono-, di-, tri- or tetrasubstituted by methyl or ethyl or alkoxyalkyl or alkylthioalkyl with 1 to 3 carbon atoms per alkoxy and alkylthio and 2–3 carbon atoms in the alkyl part, excluding the compounds in which (a) $R^4$ represents methyl and (i) $R^1$, $R^2$ and $R^3$ represent hydrogen, or (ii) $R^1$ represents chlorine or nitro, $R^2$ represents chlorine and $R^3$ represents hydrogen, or (iii) $R^1$ represents nitro and $R^2$ and $R^3$ represent hydrogen, or (iv) $R^1$ and $R^3$ represent chlorine and $R^2$ represents hydrogen and (b) $R^4$ represents n-butyl, $R^1$ and $R^3$ represent hydrogen and $R^2$ represents chlorine.

4. An N-sulphenylated benzenesulphonic acid amide according to claim 1, in which $R^1$, $R^2$ and $R^3$ independently of one another repesent hydrogen, chlorine, nitro or methyl and $R^4$ represents methyl, ethyl, iso-propyl, n-butyl, iodopropargyl, cyclopentyl, cyclohexyl, allyl or 3-methoxy-n-propyl, excluding the compounds in which (a) $R^4$ represents methyl and (i) $R^1$, $R^2$ and $R^3$ represent hydrogen, or (ii) $R^1$ represents chlorine or nitro, $R^2$ represents chlorine and $R^3$ represents hydrogen, or (iii) $R^1$ represents nitro and $R^2$ and $R^3$ represent hydrogen, or (iv) $R^1$ and $R^3$ represent chlorine and $R^2$ represents hydrogen, and (b) $R^4$ represents n-butyl, $R^1$ and $R^3$ represent hydrogen and $R^2$ represents chlorine.

5. An N-sulphenylated benzenesulphonic acid amide according to claim 1, wherein such amide is N-ethyl-N-dichlorofluoromethylsulphenyl-benzenesulphonamide of the formula

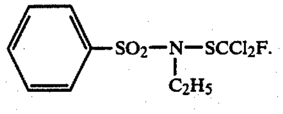

6. An N-sulphenylated benzenesulphonic acid amide according to claim 1, wherein such amide is 4-methyl-3-nitro-(N-dichlorofluoromethylsulphenyl-N-methyl)-benzenesulphonamide of the formula

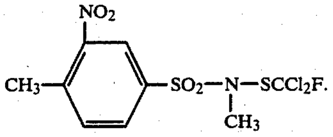

7. An N-sulphenylated benzenesulphonic acid amide according to claim 1, wherein such amide is 4-nitro-(N-dichlorofluoromethylsulphenyl-N-methyl)-benzenesulphonamide of the formula

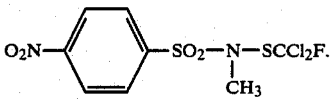

8. An N-sulphenylated benzenesulphonic acid amide according to claim 1, wherein such amide is 4-nitro-(N-dichlorofluoromethylsulphenyl-N-n-butyl)-benzenesulphonamide of the formula

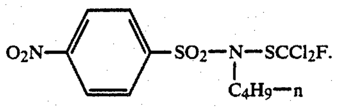

9. An N-sulphenylated benzenesulphonic acid amide according to claim 1, wherein such amide is 2,5-dimethyl-(N-dichlorofluoromethylsulphenyl-N-methyl)-benzenesulphonamide of the formula

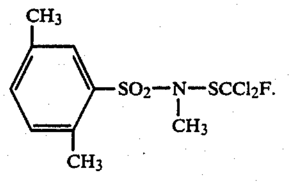

10. The method according to claim 2, wherein such compound is

N-ethyl-N-dichlorofluoromethylsulphenyl-benzenesulphonamide, 4-methyl-3-nitro-(N-dichlorofluoromethylsulphenyl-N-methyl)-benzenesulphonamide, 4-nitro-(N-dichlorofluoromethylsulphenyl-N-methyl)-benzenesulphonamide, 4-nitro-(N-dichlorofluoromethylsulphenyl-N-n-butyl)-benzenesulphonamide or 2,5-dimethyl-(N-dichlorofluoromethylsulphenyl-N-methyl)-benzenesulphonamide.

11. A fungicidal composition comprising a fungicidally effective amount of a compound according to claim 1 in admixture with a diluent.

* * * * *